United States Patent
Gotch et al.

(10) Patent No.: US 6,648,845 B1
(45) Date of Patent: Nov. 18, 2003

(54) METHOD AND APPARATUS FOR DETERMINING HEMODIALYSIS PARAMETERS

(75) Inventors: Frank A. Gotch, San Francisco, CA (US); Thomas I. Folden, Alamo, CA (US)

(73) Assignee: Fresenius Medical Care North America, Lexington, MA (US)

( * ) Notice: Subject to any disclaimer, the term of this patent is extended or adjusted under 35 U.S.C. 154(b) by 0 days.

(21) Appl. No.: 09/003,798

(22) Filed: Jan. 7, 1998

(51) Int. Cl.$^7$ ............................................. A61M 37/00
(52) U.S. Cl. ..................... 604/5.01; 604/4.01; 600/505; 210/646
(58) Field of Search ................. 604/4.01, 5.01–5.04, 604/6.09, 6.1, 6.11, 6.16, 500, 503–504; 422/44, 48, 68.1, 79, 82.01–82.03, 82.12; 210/645–47, 650–52, 739, 767, 252, 251.1–251.2, 258, 321.6, 321.71–321.72, 321.75, 348, 416.1, 418, 424, 433.1, 434, 437, 446, 500.21, 929; 128/898, 905; 73/861, 195–97, 866.3, 866.5; 137/825, 833, 109–110, 112; 600/454, 459, 462, 465–68, 481, 483, 485–86, 504, 505, 507

(56) References Cited

U.S. PATENT DOCUMENTS

| | | |
|---|---|---|
| 4,508,622 A | 4/1985 | Polaschegg |
| 4,923,613 A | 5/1990 | Chevallet |
| 5,024,756 A | 6/1991 | Sternby |
| 5,100,554 A | 3/1992 | Polaschegg |
| 5,312,550 A | 5/1994 | Hester |
| 5,453,576 A | 9/1995 | Krivitski |
| 5,507,723 A | 4/1996 | Keshaviah |
| 5,510,716 A | 4/1996 | Buffaloe, IV et al. |
| 5,510,717 A | 4/1996 | Buffaloe, IV et al. |
| 5,518,623 A | 5/1996 | Keshaviah et al. |
| 5,567,320 A | 10/1996 | Goux |
| 5,570,026 A | 10/1996 | Buffaloe, IV et al. |

(List continued on next page.)

FOREIGN PATENT DOCUMENTS

| | | |
|---|---|---|
| EP | 0 547 025 A1 | 6/1993 |
| EP | 0 330 892 B1 | 7/1994 |
| EP | 0 547 025 B1 | 6/1996 |
| WO | WO 9608305 A1 | 3/1996 |

OTHER PUBLICATIONS

Krivitski, Nikolai M., "Theory and Validation of Access Flow Measurement by Dilution Technique During Hemodialysis," *Kidney International*, vol. 48, 1995, pp. 244–250.

Bosman, Peter J., et al., "Access Flow Measurements in Hemodialysis Patients: In Vivo Validation of an Ultrasound Dilution Technique," *Journal of the American Society of Nephrology*, vol. 7, No. 6, 1996, pp. 966–969.

*Primary Examiner*—Angela D. Sykes
*Assistant Examiner*—Patricia Bianco
(74) *Attorney, Agent, or Firm*—Gibson, Dunn & Crutcher LLP

(57) ABSTRACT

This invention provides a method and apparatus for calculating a hemodialysis parameter, especially blood access flow rate, using multiple dialysance values. The dialysance values may be calculated based upon either sodium or urea concentrations. One dialysance value can be determined for conditions in which a patient's arterial line withdraws blood from an upstream location in a patient's fistula and treated blood is returned by a venous line to a downstream location in a patient's fistula. The second dialysance value can be determined when the lines have been reconfigured so that the arterial line withdraws blood from a downstream portion of a patient's fistula and the venous line returns treated blood to an upstream portion of a patient's fistula. Since it is possible to determine the dialysance values solely from concentration measurements made on the dialysate side of the dialysis apparatus, the present method and apparatus provide a non-invasive means for determining hemodialysis parameters such as blood access flow rate and recirculation.

9 Claims, 4 Drawing Sheets

U.S. PATENT DOCUMENTS

| | | |
|---|---|---|
| 5,595,182 A | 1/1997 | Krivitski |
| 5,644,240 A | 7/1997 | Brugger |
| 5,662,806 A | 9/1997 | Keshaviah et al. |
| 5,685,989 A | 11/1997 | Krivitski et al. |
| 5,830,365 A * | 11/1998 | Schneditz .................. 210/739 |
| 5,894,011 A * | 4/1999 | Prosl et al. ................... 422/44 |
| 6,126,831 A * | 10/2000 | Goldau et al. .............. 210/646 |
| 6,177,049 B1 * | 1/2001 | Schnell et al. ................ 422/44 |

\* cited by examiner

METHOD AND APPARATUS FOR DETERMINING HEMODIALYSIS PARAMETERS

FIELD OF THE INVENTION

This invention relates to a method and apparatus for determining hemodialysis parameters in a dialysis system, especially blood access flow rates and recirculation. More particularly, the invention relates to the calculation of hemodialysis parameters from multiple dialysance measurements. According to one method, a first dialysance measurement is made when the arterial and venous lines running from the patient to the dialyzer are in a first orientation and a second dialysance measurement is made when the arterial and venous lines are switched or reconfigured so they are in a second orientation. The invention includes a method for determining hemodialysis parameters in a non-invasive manner. The invention also provides a dialysis apparatus which includes a fluid conduit set for reconfiguring the arterial and venous lines between the first and second orientations, thereby providing an automated apparatus for determining hemodialysis parameters.

BACKGROUND OF THE INVENTION

Hemodialysis (or simply dialysis) is a process which employs an artificial kidney to aid patients whose renal function has deteriorated to the point where their body cannot adequately rid itself of toxins. In hemodialysis a dialyzer is used which contains a semi-permeable membrane, the membrane serving to divide the dialyzer into two chambers. Blood is pumped through one chamber and a dialysis solution through the second. As the blood flows by the dialysis fluid, impurities, such as urea and creatinine, diffuse through the semi-permeable membrane into the dialysis solution. The electrolyte concentration of the dialysis fluid is set so as to maintain electrolytic balance within the patient.

Further purification in an artificial kidney is possible through ultrafiltration. Ultrafiltration results from the normal situation wherein there is a positive pressure differential between the blood and the dialysis fluid chambers. This pressure differential causes water in the blood to pass through the membrane into the dialysis solution. This provides the benefit of reducing a dialysis patient's excess water load which normally would be eliminated through proper kidney functioning.

Typically, an arterio-venous shunt, frequently termed a "fistula," is surgically inserted between a patient's artery and vein to facilitate transfer of blood from the patient to the dialyzer. During a normal dialysis treatment, one end of an arterial line or tube is inserted into the upstream end of the fistula (i.e., at a point near the patient's artery) and transports blood withdrawn from the upstream portion of the fistula to the inlet of the dialyzer; a venous line or tube connected to the output of the blood side of the dialyzer returns treated blood to the fistula at an insertion point downstream of the arterial line (i.e., at a point nearer the patient's vein).

Successful dialysis treatment requires knowledge of several hemodialysis parameters in order to optimize the overall efficacy of the dialysis procedure, to assess the condition of the fistula and to determine the actual purification achieved. One key measure of dialysis efficiency is described by the ratio Kt/V, where K is the clearance or dialysance (both terms representing the purification efficiency of the dialyzer), t is treatment time and V is the patient's total water volume. Studies have demonstrated that patient survival increases when the Kt/V ratio has a value of 0.8 or greater (Gotch, F. A. & Sargent, S. A. "A Mechanistic Analysis of the National Cooperative Dialysis Study." Kidney International., Vol. 28, pp. 526–34 (1985)). The water volume of the patient, V, can be estimated from a patient's weight, age, sex and percentage of body fat. Hence, with knowledge of clearance, K, it is possible to determine the time, t, for optimal dialysis treatment according to the above relationship.

Dialysance or clearance, as noted above, is a measure of the purification efficiency of the dialyzer. More specifically, dialysance is a measure of the volume of blood cleared of urea or some other solute within a certain time period. Hence, one way to determine dialysance is to make in-vivo urea concentration measurements. This is a time-consuming approach, since it requires that samples be withdrawn and analyzed in a laboratory. Alternatively, sodium chloride dialysance or clearance can be measured, since it is known that the clearance of sodium chloride is equivalent to urea clearance. Because sodium and chloride ions comprise essentially all the electrolytes giving rise to the conductivity of both blood and the dialysis solution, dialysance or clearance can simply be determined by making conductivity measurements.

As shown by Sargent, J. A. and Gotch, F. A. ("Principles and Biophysics of Dialysis," in: Replacement of Renal Function by Dialysis, (W. Drukker, et al., Eds.), Nijoff, The Hague (1983) incorporated herein by reference), it is possible to define dialysance in terms of concentrations at the inlet and outlet to the blood side of the dialyzer, the inlet to the dialysis solution side of the dialyzer and the blood flow rate according to the following equation:

$$D = Qb \cdot \frac{Cbi - Cbo}{Cbi - Cdi} \qquad (1)$$

where:
 Cbi=blood inlet concentration
 Cbo=blood outlet concentration
 Qb=blood flow rate
 D=dialysance
 Cdi=dialysis fluid inlet concentration
 Cdo=dialysis fluid outlet concentration As demonstrated in U.S. Pat. No. 5,100,554 to Polaschegg, this equation can be rewritten strictly in terms of dialysis solution concentrations. In particular, from mass balance based upon flow across the dialysis membrane, the following relationship can be established:

$$Qb(Cbi-Cbo) = -Qd(Cdi-Cdo) \qquad (2)$$

Thus, it is possible from equations (1) and (2) to rewrite equation (1) without a Cbo term as follows:

$$D = -Qd \cdot \frac{Cdi - Cdo}{Cbi - Cdi} \qquad (3)$$

where:
 Qd=dialysis flow rate; the rest of the terms are as defined for equation (1).

In equation (3), the terms Qd and Cdi are known and a value for Cdo can be easily determined by placing a detector at the dialysis solution outlet of the dialyzer. This leaves D and Cbi as the only unknown values. Using two dialysis solutions having different initial concentrations of a substance, it is possible to write two equations with two unknowns and solve for dialysance, as shown in the following equation:

$$D = Qd \cdot \frac{(Cdi1 - Cdo1) - (Cdi2 - Cdo2)}{Cdi1 - Cdi2} \quad (4)$$

where:
D=dialysance
Qd=dialysis flow rate
Cdi1=concentration of substance upstream of dialyzer, first dialysis solution
Cdo1=concentration of substance downstream of dialyzer, first dialysis solution
Cdi2=concentration of substance upstream of dialyzer, second dialysis solution
Cdo2=concentration of substance downstream of dialyzer, second dialysis solution Other methods and apparatus for determining dialysance are described in U.S. Pat. No. 5,024,756 to Sternby, U.S. Pat. No. 5,567,320 to Goux, and U.S. Pat. No. 4,668,400 to Veech, as well as European Patents EP 330,892 B1 and EP 547,025 B1 to Sternby and European Patent Application 547,025 A1 by Sternby.

Blood access flow rate is another hemodialysis parameter which is of critical importance in optimizing dialysis procedures and in monitoring the general condition of the fistula. Blood access flow rate is defined as the blood flow rate at the entrance to the fistula as the blood flows in from a patient's artery. Blood access flow rate is important for at least two reasons. First, with time it is possible for the fistula to become clotted or stenose. Hence, flow rate can serve as an indicator of changes in the integrity of the fistula. Secondly, the rate of access flow relative to dialyzer flow rate affects recirculation, the phenomenon whereby treated blood from the venous line commingles with untreated blood in the fistula and is drawn into the arterial line and then carried back to the dialyzer. It can readily be appreciated that as recirculation increases the efficiency of the dialysis procedure decreases, since recirculation results in treated blood being retreated. Recirculation increases when the blood flow rate through the fistula is insufficient relative to the blood flow rate through the dialyzer. Thus, a knowledge of access flow rate is also important in assessing the degree to which recirculation occurs and in selecting flow rates for pumping blood through the dialyzer.

Several methods are known for determining access flow rates. However, these methods all suffer from a critical limitation, namely that the determination depends upon blood concentrations of some solute or added solution. As a consequence, the methods are invasive, tending to require the withdrawal of blood samples or the injection of solutions into the patient's blood stream.

One such method, the color-coded duplex sonography method has found utility in identifying patients at risk for access failure (Sands, J. et al., "The Effect of Doppler Flow Screening Studies and Elective Revisions on Dialysis Failure." ASAIO Journal, Vol. 38, pp. 524–527 (1992)). The method, however, is only rarely used because of its expense, the requirement for trained personnel and the fact that results vary depending upon operating conditions (see for example, Wittenberg, G. et al. "Interobserver Variability of Dialysis Shunt Flow Measurements using Color Coated Duplex Sonography." Rofo Fortschr Geb Rontgenstr Neuen Bildgeb Verfahr, Vol. 154, pp. 375–378 (1993) and Oates, C. P., et al. "The use of Diasonics DRF400 Duplex Sound Scanner to Measure Blood Flow in Arteriovenous/Fistulae in Patients Undergoing Hemodialysis: An Analysis of Measurement Uncertainties." Ultrasound Med. Biol., Vol. 16, pp.571–579, (1990)).

Other approaches are based upon dilution methods and require the injection of a volume of a solution having a characteristic distinct from blood (often called a "bolus") into either the arterial or venous line which is connected to the patient's fistula. A general method for determining flow rates in tubes is described in U.S. Pat. No. 5,644,240 by Brugger. This method involves the injection of a saline bolus and the subsequent monitoring of changes in electrical conductivity in a patient's blood line.

A related method requires the reversal of the arterial and venous lines so that the venous line is upstream of the arterial line, the injection of a saline bolus into one of the blood lines and then detection of the alteration of the sound velocity characteristics of the blood by ultrasound methods. This method is described in: U.S. Pat. Nos. 5,685,989, 5,595,182 and 5,453,576 to Krivitski; PCT application WO 96/08305 A1 by Krivitski; and in a publication by Nikolai Krivitski ("Theory and Validation of Access Flow Measurement by Dilution Technique during Hemodialysis." Kidney International, Vol. 48, pp. 244–250 (1995)). These methods suffer from their invasive nature, namely the requirement that a foreign mixture be injected into the patient's bloodstream and, in some cases, the insertion of sensors into a patient's vascular system (U.S. Pat. Nos. 5,595,182 and 5,453,576 to Krivitski). Furthermore, the injection requirement for these methods makes these approaches relatively cumbersome; such methods also do not lend themselves to automation.

There are similar shortcomings to current methods for calculating recirculation. Like methods for determining blood access flow rates, present procedures require measurements on the blood side of the dialyzer and thus are invasive in nature. Often the methods require injection of a foreign solution into the blood stream (U.S. Pat. Nos. 5,570,026, 5,510,717 and 5,510,716 to Buffaloe, IV, et al.; U.S. Pat. No. 5,644,240 to Brugger; U.S. Pat. No. 5,685,989 to Krivitski, et al., U.S. Pat. Nos. 5,595,182 and 5,453,576 to Krivitski; and U.S. Pat. No. 5,312,550 to Hester).

In contrast to these invasive techniques, a method using dialysis solution concentration measurements only has been developed to determine a patient's blood sodium level (U.S. Pat. No. 4,923,613 to Chevallet). Related methods have been developed in which the effect of variations in solute concentration in dialysis solutions are determined. Results are used to develop a profile to optimize dialysis conditions to the patient's needs (U.S. Pat. Nos. 5,662,806 and 5,518, 623 to Keshaviah, et al. and U.S. Pat. No. 5,507,723 to Keshaviah).

Several dialysis apparatus have been developed to monitor changes in dialysis solution composition, including U.S. Pat. No. 4,508,622 to Polaschegg and U.S. Pat. No. 5,024, 756 to Sternby and European Patents 097,366 A2 to Polaschegg; 330,892 B1 and 547,025 B1 to Sternby; as well as European Patent Application 272,414 A2 to Polaschegg.

However, there remains a need for a method and apparatus for determining hemodialysis parameters such as blood access flow rates and recirculation by non-invasive methods that do not require that measurements be made on the blood side of the dialyzer. The methods and apparatus of the present invention satisfy such a need by providing for the first time an approach for determining hemodialysis parameters such as blood access flow rate and recirculation solely from concentration measurements taken on the dialysate side of the dialyzer, thereby providing a non-invasive means for determining such parameters.

SUMMARY OF THE INVENTION

In general, the invention provides an apparatus and a method for accurately, reliably and inexpensively determining hemodialysis blood parameters such as blood access flow rate and recirculation from multiple dialysance values using a non-invasive method and apparatus, whereby it is unnecessary to inject a foreign solution or to insert intravascular sensors into a patient's bloodstream in order to make the determination.

More specifically, this invention provides a dialysis apparatus which includes a novel fluid conduit set for reconfiguring the orientation of a patient's arterial and venous lines between a first and second orientation. In the first orientation, the arterial line carries blood from an upstream portion of a patient's fistula and the venous line carries blood to a downstream portion of the fistula; in the second orientation, the arterial line carries blood from a downstream portion of a patient's fistula and the venous line carries blood to an upstream portion of the fistula. Thus, the invention provides an automated dialysis apparatus for determining hemodialysis parameters from multiple dialysance measurements, such parameter preferably being blood access flow rate or recirculation. In addition to the fluid conduit set, the apparatus includes at least one detector located in a dialysis solution line for monitoring the concentration of a substance in the dialysis fluid. Using the detector(s) to monitor the concentration of the substance upstream and downstream of the dialyzer, it is possible through the method described herein to determine dialysance values for the first and second orientation and, ultimately, a value for a hemodialysis parameter such as blood access flow rate or recirculation. Alternatively, the detector may only be used to measure the concentration of a substance in the dialysis solution at a point downstream of the dialyzer when it is possible to calculate dialysance from a single downstream measurement; this is the case, for example, when urea concentrations are measured.

The fluid conduit set provided for in the invention is designed to be used in a dialysis apparatus and provides a system for reconfiguring blood flow through a dialysis patient's arterial and venous lines. In particular, the fluid conduit set has a first and second fluid path. The first fluid path routes blood flow so that the arterial line carries blood withdrawn from an upstream portion of a patient's fistula and the venous line carries blood toward a downstream portion of the fistula; the second fluid path directs blood flow so that the arterial line carries blood withdrawn from a downstream portion of the fistula and the venous line carries blood toward an upstream portion of the fistula.

In addition to the dialysis apparatus, this invention also includes methods for determining hemodialysis blood parameters from multiple dialysance values, which preferably can be determined in a non-invasive way. More specifically, this invention provides methods for determining blood access flow rate and recirculation solely from multiple dialysance values. The methods of the invention may be automated using the fluid conduit set and have the additional advantage of being able to be performed with simple and inexpensive equipment. Moreover, the reproducibility and accuracy of the method is comparable to the dilution methods described above.

The non-invasive methods provided by the invention generally involve determining a first dialysance value for a dialysis session during which the arterial and venous lines are initially in the first orientation. A second dialysance value is then determined for conditions in which the arterial and venous lines are in the second orientation. The arterial and venous lines may be manually switched or reconfigured; most preferably, the reconfiguring is automated using the fluid conduit set provided in this invention.

When this general approach is utilized, the multiple dialysance values used to calculate a hemodialysis parameter may be determined in any of a number of ways, including, for example, those described in the U.S. and European patents listed above. However, most advantageously, the multiple dialysance value are determined using the non-invasive method described earlier in which dialysis solutions having different initial concentrations of a substance are successively flowed through the dialyzer and the concentration of the substance in each solution measured at points upstream and downstream of the dialyzer. These concentration measurements can then be used to calculate dialysance according to equation (4). Most preferably, in this embodiment of the invention, the concentration of the substance being measured is sodium chloride, and the concentration is determined using a conductivity detector.

A second non-invasive method for determining dialysance is to monitor urea concentrations in the dialysate downstream of the dialyzer using an urea monitor. Regardless of how the dialysance values are determined, dialysance values for the first and second orientation can then be utilized to calculate a hemodialysis parameter such as blood access flow rate as described more fully below.

The invention also provides a second approach for determining a blood parameter from multiple urea dialysance values. In this embodiment, a value for urea dialysance is determined based upon urea concentrations in samples acquired while the arterial and venous lines are in the second orientation. A value for effective urea dialysance is determined from values for urea dialysance in conjunction with a patient's systemic urea concentration and the urea concentration at the dialyzer blood inlet. The values determined for urea dialysance and effective urea dialysance can then be used to calculate a hemodialysis parameter. Most preferably, such parameter is blood access flow rate or recirculation. In this embodiment of the invention, the arterial and venous lines may also be switched or reconfigured manually; most preferably, the reconfiguring is automated using the fluid conduit set provided for by this invention.

DETAILED DESCRIPTION OF THE PREFERRED EMBODIMENTS

Apparatus for Automated Determination of Hemodialysis Parameters

Figure 1:
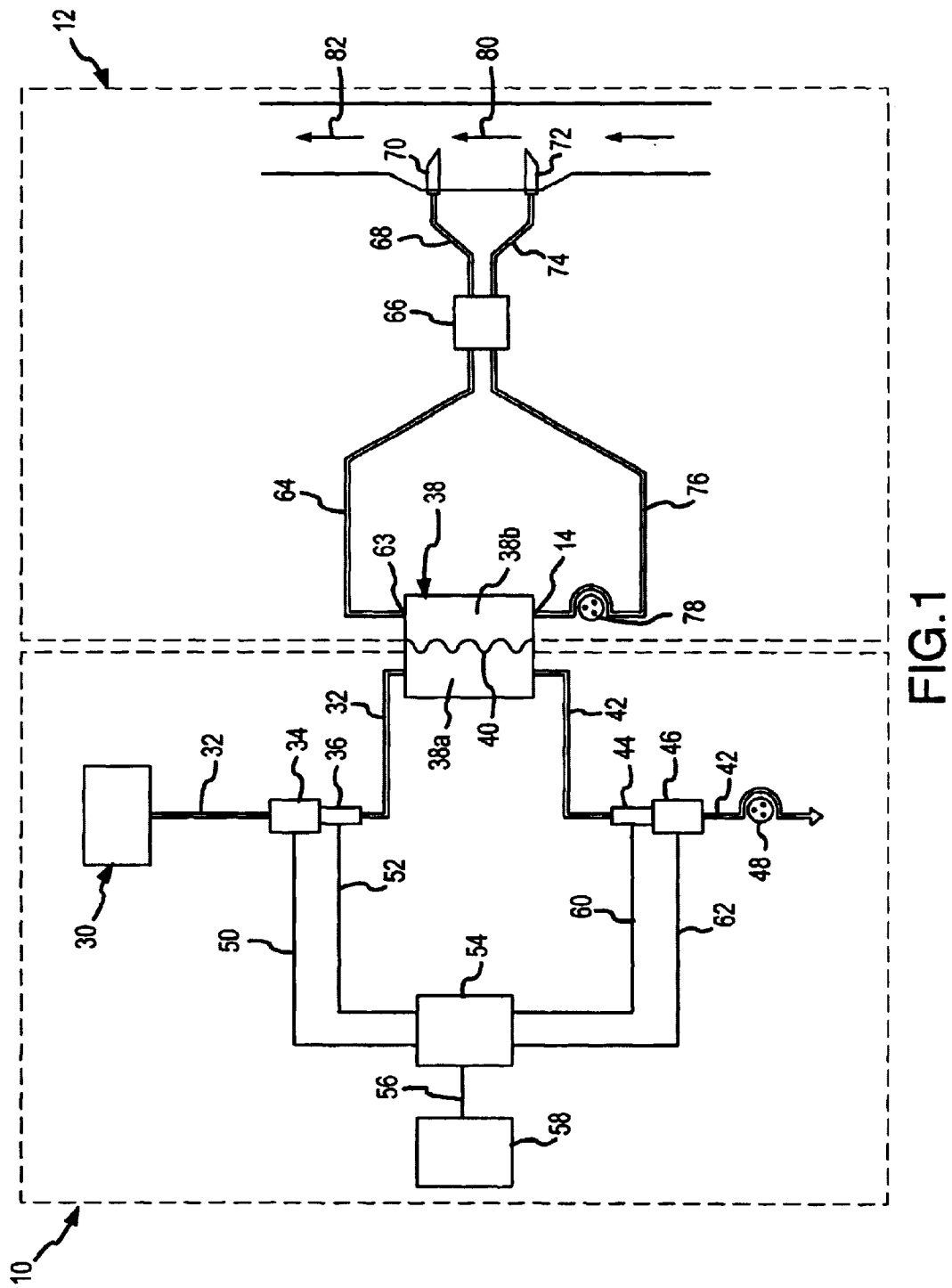
FIG. 1 is a schematic representation of a dialysis apparatus including a fluid conduit set which enables the reconfiguring of the arterial and venous lines between the first and second orientation to be automated.

Aspects of the current dialysis apparatus are illustrated in FIG. 1. In its most general form, the dialysis apparatus includes a dialysate side 10 and a blood side 12. More specifically, the dialysate side 10 of the dialysis apparatus comprises: a dialysis solution source 30; the dialysis solution side 38a of a dialyzer 38; a dialysis solution line comprising a dialysis solution inlet line 32 and a dialysis solution outlet line 42; and a pump 48 for drawing dialysis fluid through the dialyzer 38. The blood side 12 of the dialysis apparatus comprises: an arterial line 76, a venous line 64, the blood side 38b of the dialyzer 38; a pump 78 for drawing blood through the arterial line 76, into the dialyzer 38 and finally into the venous line 64; and a fluid conduit set 66 which facilitates the reconfiguring of the arterial and venous lines 76, 64 between a first and second orientation.

Figure 2:
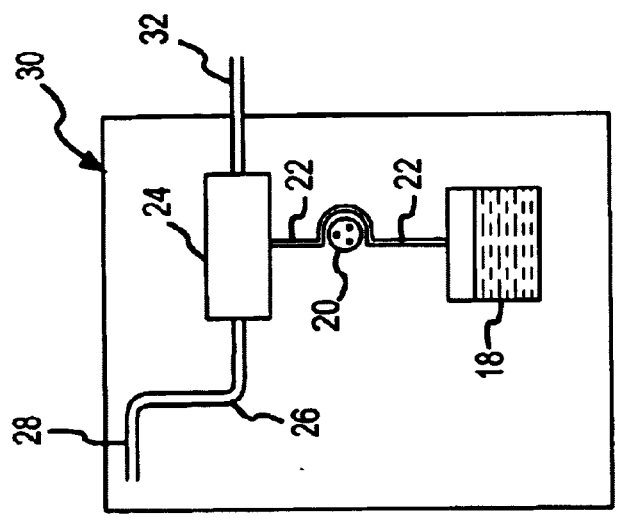
FIG. 2 is a schematic representation which shows in more detail the structure of the dialysis solution source of a dialysis apparatus.

The dialysis solution source 30 may simply be a container of premixed solution. More preferably, as shown in FIG. 2, the dialysis solution source 30 includes a mixer 24 which can generate a dialysis solution having a desired concentration of different substances. The mixer 24 (not detailed) is separately connected by a concentrate line 22 to a concentrate tank 18 and by a fresh water supply line 26 to a fresh water supply 28. The concentrate tank 18 contains concentrate, wherein concentrate is a concentrated form of the substance(s) to be mixed with fresh water to prepare a dialysis solution. A pump 20 may be interposed between the concentrate tank 18 and the mixer 24 for pumping concentrate to the mixer 24. Fresh water and concentrate are combined in the mixer 24 to yield a desired dialysis solution having a predetermined concentration of at least one substance. In a preferred embodiment, the substance is a sodium salt, most preferably sodium chloride. The mixer 24 may further include a heater (not shown) for heating fresh water to a temperature approximating that of a dialysis patient's blood and a means for degassing dialysis solution (not shown). The mixer 24 may also be connected to more than one tank of concentrate (not shown) in those cases where multiple substances are to be mixed into the dialysis solution and it is advantageous to have separate concentrates.

The dialysis solution source may also be electrically connected to a control unit (not shown) which electronically regulates the composition of the dialysis solution so that dialysis solutions having particular concentrations of various solutes can be prepared.

In one embodiment of the invention (FIG. 1), a pump 48 located downstream of the mixer 30 in the dialysis solution outlet line 42 draws the prepared dialysis solution through a dialysis solution inlet line 32 to an upstream detector 34, located in the dialysis solution inlet line 32. The upstream detector 34 measures an upstream concentration parameter of at least one substance in the dialysis solution (first or upstream measurement). Preferably the upstream detector 34 is a conductivity meter and measures sodium salt concentration, since typically such salts comprise approximately 90% or more of the electrolytes affecting conductivity of the dialysis solution. However, the substance being measured could include any marker in the dialysis solution or any waste product capable of exchanging across a dialysis membrane. Examples of waste products that could be monitored include urea and creatinine; examples of added markers include dextrose, oxygen or a dye. When conductivity is measured, the upstream concentration may be temperature-corrected using a first temperature detector 36 which is located in the dialysis solution inlet line 32 downstream from the upstream detector 34.

Dialysis solution continues through a dialysis fluid chamber (second chamber) 38a of a dialyzer 38, separated from the blood chamber (first chamber) 38b by a semipermeable membrane 40, and through a dialysis solution outlet line 42 to a downstream detector 46. The downstream detector 46 measures the downstream concentration parameter of a substance in the dialysis solution, where the substance preferably is the same substance which was measured by the upstream detector 34 (second or downstream measurement). Again, preferably such substance is sodium salts, and most preferably is sodium chloride. A second temperature detector 44 connected to the dialysis solution outlet line 42 and located upstream of the downstream detector 46 can be used to temperature-correct conductivity measurements if the downstream detector 46 is a conductivity meter.

The detectors 34, 46 can be any detector capable of measuring the concentration of a substance in dialysis solution. Such detectors include, for example, those capable of making conductivity, electrochemical, total spectrographic or magnetic measurements. The detectors 34, 46 may include an ion-selective electrode. As noted above, preferably, the upstream detector 34 and the downstream detector 46 are conductivity meters. Each detector 34, 46 is electrically connected by signal lines 50, 52, 60, 62 to a comparator 54, so that a representation of the first and second measurement can be transferred to the comparator 54. The comparator 54 may provide a readout of the first and second concentration measurements; most preferably, comparator 54 evaluates the first and second measurements and provides a readout of the concentration difference between the upstream and downstream locations. Alternatively, the comparator 54 may be electrically connected by a signal line 56 to a difference unit 58 which evaluates the first and second measurements and provides a readout of the concentration difference.

Figure 3:
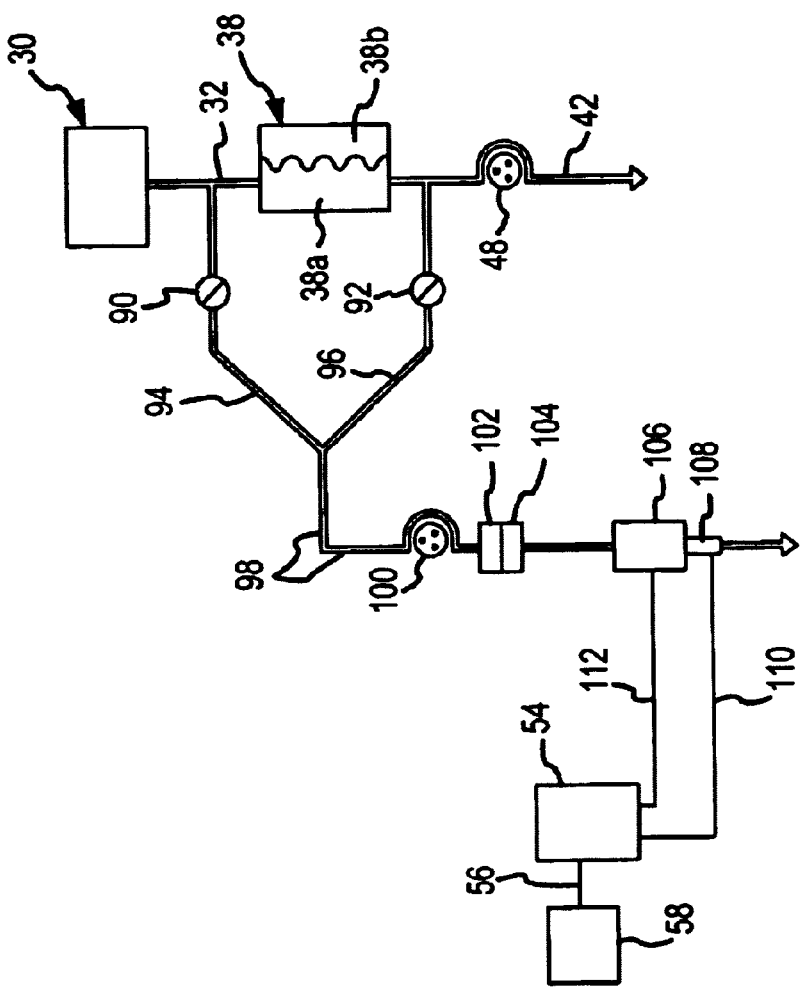
FIG. 3 is a schematic representation of a modified form of the dialysis apparatus shown in FIG. 1 wherein there is a single detector rather than two.

Another embodiment (FIG. 3) of the invention provides a dialysis system in which a single detector 106 can make both upstream and downstream concentration measurements. Common features to the embodiment described in FIG. 1 retain the same numbers. In this embodiment, there is a single detector 106 connected to both the dialysis solution inlet line 32 and the dialysis solution outlet line 42. This apparatus has a dialysis solution source 30 as described above. The inlet line 32 is connected to a first branch line 94, which is interposed between the dialysis solution source 30 and the dialysis solution side 38a of the dialyzer 38. Similarly, the dialysis solution outlet line 42 is connected to a second branch line 96. Since the dialysis solution pump 48 creates a vacuum in the dialysis solution inlet and outlet lines 32, 42, shut off valves 90, 92 are provided in the first and second branch lines 94, 96 to regulate flow through the branch lines. The first and second branch lines 94, 96 both connect at a detector inlet line 98 which is connected to the detector 106. The detector 106 is of the same type as described above and may also be connected to a temperature correction detector 108 located downstream of the detector 106. The detector 106 is further electrically connected via signal line 112 to the comparator 54 and is capable of transmitting to the comparator a representation of the measured concentrations of substance in the dialysis solution. Temperature correction detector 108 is similarly connected to the comparator 54 by signal line 110.

By alternately opening the shut off valves 90, 92 in either the first or second branch line 94, 96, it is possible to expose the detector 106 alternatively to upstream or downstream dialysis solution using a pump 100 located in the detector inlet line 98 to overcome the vacuum created in the dialysis solution inlet and outlet lines 32, 42 by the dialysis solution pump 48. A storage reservoir 104 is placed in detector inlet line 98 downstream of the pump 100 and includes a means for providing pressure compensation, such as through an opening 102 in the storage reservoir 104.

In a related embodiment, the dialysis apparatus may again include a single detector. In this case, the apparatus is as shown in FIG. 1, except that the upstream detector 34 and the first and second temperature detectors 36, 44 and their associated signal lines 50, 52 and 60 are omitted. In this case, the downstream detector 46 serves as the only detector. This design is appropriate when it is necessary to only monitor the concentration of a substance in the dialysis solution at a point downstream of the dialyzer 38 in order to determine dialysance. Such is the case with urea, as described more fully below. This arrangement would also be appropriate in cases where the concentration of the substance in the dialysis solution downstream of the dialyzer is compared with a set or reference value for the substance at the upstream location.

As shown in FIG. 1, the blood side 12 of the present dialysis apparatus in its simplest form comprises a patient's fistula 82, an arterial line 76, the blood side 38b of the dialyzer 38, a venous line 64 and a fluid conduit set 66. As used here, fistula is defined to include any arterio-venous shunt located between a patient's artery and vein (not shown). The fistula may be made of synthetic materials or animal tissue. Blood flow through the fistula 82 is in the direction of the arrows 80, i.e. moving from the artery toward the vein. One end of each of the arterial line 76 is connected to the inlet 79 of the blood chamber of the dialyzer; one end of the venous line 64 is connected to the outlet 63 of the blood side of the dialyzer. The other end of the arterial and venous lines 76, 64 are connected to the fluid conduit set 66.

The blood side 12 of the present dialysis apparatus may also include a first transfer line 74 and a second transfer line 68. One end of each of the first and second transfer line 74, 68 is connected to a first and second needle/catheter 72,70, respectively, to facilitate insertion of the first and second transfer line 74, 68 into the patient's fistula 82. The second end of each of the first and second transfer lines 74, 68 is connected to the fluid conduit set 66. As noted above, one end of each of the arterial and venous lines 76, 64 are also attached to the fluid conduit set 66.

Figure 4B:
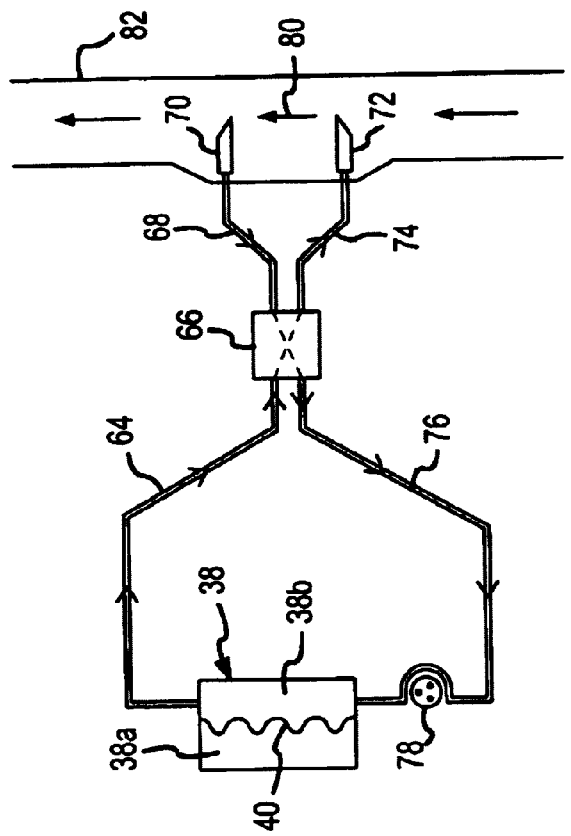
FIG. 4B is a schematic representation of the blood flow through the blood side of the dialyzer in the second orientation.
Figure 4A:
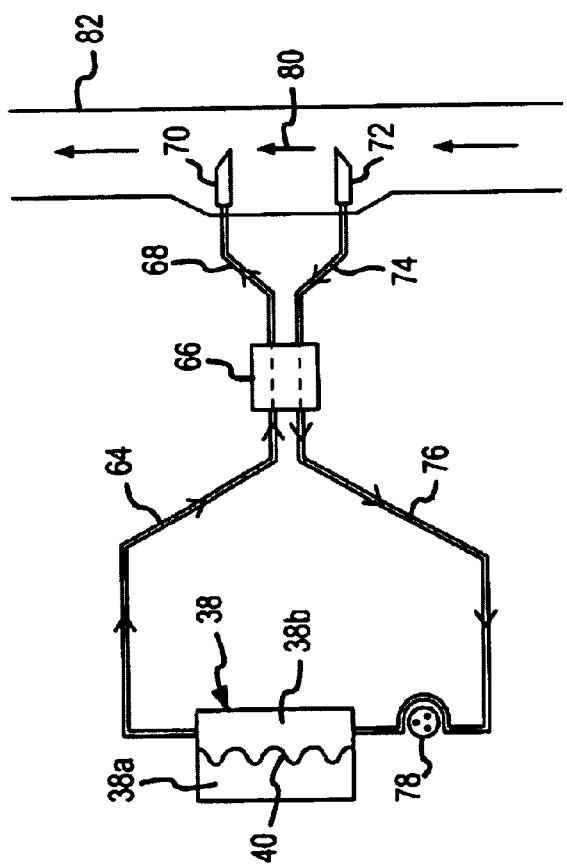
FIG. 4A is a schematic representation of the blood flow through the blood side of the dialyzer in the first orientation.

Preferably, the fluid conduit set 66 has a first and second fluid path. The first fluid path routes the blood as shown in FIG. 4A (the numbering of FIG. 1 is retained). In this case, blood is withdrawn by the action of pump 78 from an upstream portion of a patient's fistula (blood flow through the fistula 82 is indicated by arrow 80) and is carried successively through the first transfer line 74, the fluid conduit set 66, the arterial line 76, and then into the blood side 38b of the dialyzer 38. As the blood flows through the dialyzer 38, contaminants in the blood exchange across the dialysis membrane 40 with dialysis solution flowing through the dialysis solution side 38a of the dialyzer. The blood then continues through the venous line 64, the fluid conduit set 66, the second transfer line 68, and finally returns to a downstream portion of the fistula. The second fluid path causes the blood to travel as shown in FIG. 4B (again, the numbering is the same as in FIG. 1). In this configuration, the fluid conduit set establishes a path in which blood is withdrawn from a downstream portion of the patient's fistula, passes through the second transfer line 68 into the fluid conduit set 66 and then through the arterial line 76 into the blood side 38b of the dialyzer 38. After traveling through the blood side 38b of the dialyzer 38, the blood flows through the venous line 64 back into the fluid conduit set 66, which then routes the blood into the first transfer line 74 and finally to an upstream portion of the fistula.

Calculation of Hemodialysis Parameters Based Upon Sodium Concentration

Figure 5:
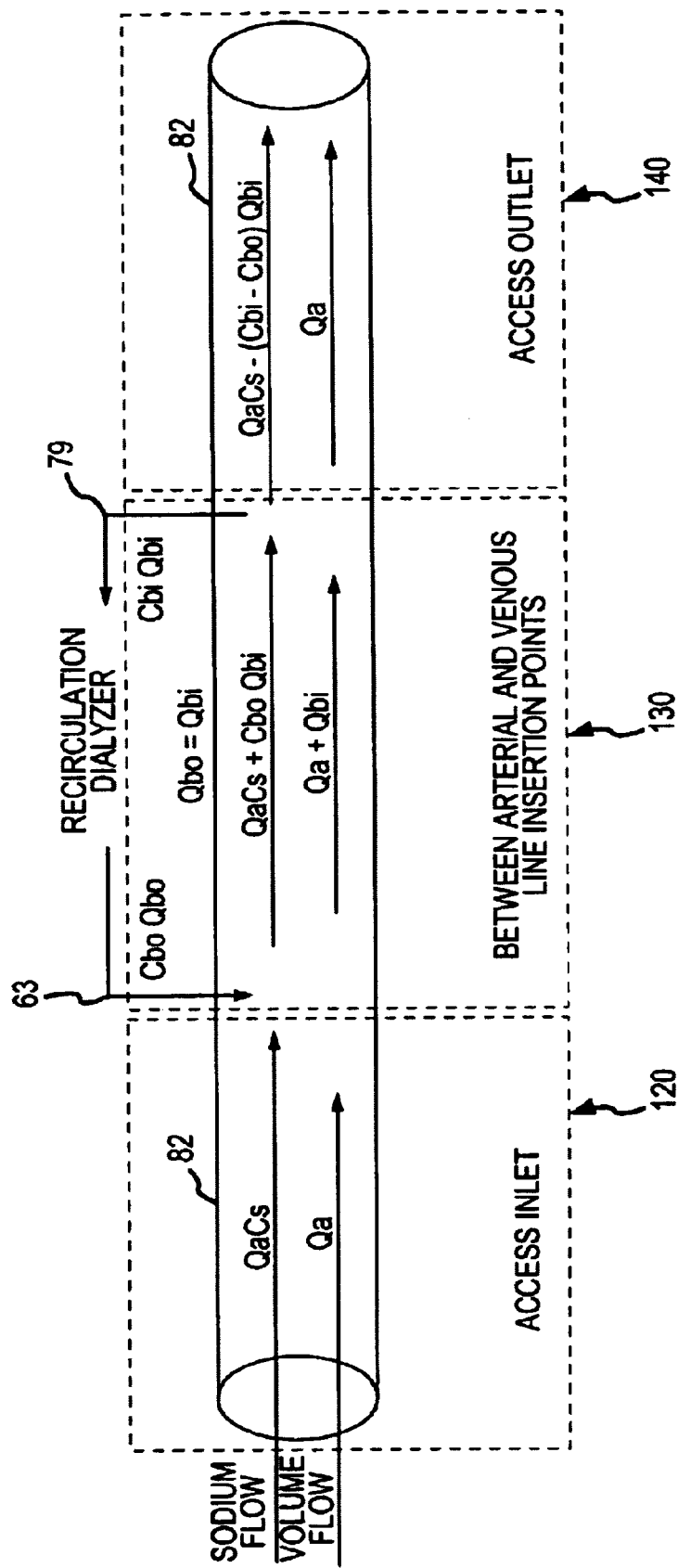
FIG. 5 is a diagrammatic representation of substance flow and volume flow through a typical fistula and dialyzer during a dialysis treatment, wherein the arterial line withdraws blood from a downstream portion of a patient's fistula and the venous line returns blood to an upstream portion of the patient's fistula (the "second orientation").

This invention provides methods for calculating hemodialysis parameters from multiple dialysance values determined using the apparatus described above. The theoretical basis of how multiple dialysance values can be utilized to calculate important hemodialysis parameters such as blood access flow rate is based upon an analysis of solute flow through a fistula when dialyzer blood flow is countercurrent to blood access flow (i.e., when the arterial and venous lines are in the second orientation) and when the ultrafiltration rate (Qf) is zero. FIG. 5 schematically represents solute flow through a fistula 82 under such conditions (the numbering in FIG. 5 is the same as in FIG. 1).

Although FIG. 5 is based upon the situation in which sodium ion concentration is measured, analogous equations can be written for other solutes utilizing the same theory outlined below. For example, similar equations for the situation where urea concentrations are monitored are listed below.

As shown in FIG. 5, sodium flow at the fistula access inlet 120 is equal to the blood access flow rate (Qa) multiplied by the systemic sodium concentration (Cs), or (Qa·Cs). The concentration of sodium at the fistula access inlet (Cai), then, is simply sodium flow divided by volume flow at the fistula access inlet, giving:

$$Cai = (Qa)(Cs)/Qa \qquad (5)$$

When the arterial and venous lines are in the second orientation, the blood flow through the venous and arterial lines is countercurrent to blood flow through the fistula (see FIG. 4B). At the dialyzer blood inlet 79, the sodium flow is equal to the concentration of sodium at the dialyzer blood inlet (Cbi) multiplied by the dialyzer blood inlet flow rate (Qbi), or (Cbi·Qbi).

At the dialyzer blood outlet 63, the sodium flow is equal to the concentration of sodium at the dialyzer blood outlet (Cbo) multiplied by the dialyzer blood outlet flow rate (Qbo), or (Cbo·Qbo). The value of (Cbo·Qbo) is equivalent to (Cbo·Qbi) since the blood flow at the dialyzer blood inlet (Qbi) and at the dialyzer blood outlet (Qbo) are the same when the ultrafiltration rate is zero.

Between the points where the arterial and venous lines are inserted 130, the sodium flow is equivalent to the sum of the sodium flow at the fistula access inlet (Qa·Cs) plus the sodium flow at the dialyzer outlet (Cbo·Qbo=Cbo·Qbi), or (Qa·Cs+Cbo·Qbi). The total flow rate in this section of the fistula is equal to the sum of access flow rate (Qa) and dialyzer flow rates (Qbo=Qbi), or (Qa+Qbi). Thus, the sodium concentration at the dialyzer blood inlet (Cbi), is equivalent to the quotient of the sodium flow and the volume flow between the points where the arterial and venous lines are inserted and can be expressed according to the following formula:

$$CbiCn = \frac{Qa \cdot CsCn + CboCn \cdot Qbi}{Qa + Qbi} \quad (6)$$

where:
Qa=access inlet flow rate
Qbi=dialyzer blood inlet flow rate
CbiCn=concentration of sodium or conductivity at the dialyzer blood inlet
CsCn=concentration of systemic sodium or conductivity at access to fistula
CboCn=concentration of sodium or conductivity at the dialyzer blood outlet At the fistula outlet 140, sodium flow is equal to the sodium flow at the access inlet ($Qa \cdot Cs$) minus the product of the difference in sodium concentration between the dialyzer blood inlet and outlet (Cbi−Cbo) and the dialyzer flow rate (Qbi), thus giving $Qa \cdot Cs-(Cbi-Cbo)Qbi$. The volume flow at the fistula outlet is equivalent to the access inlet flow rate (Qa). Hence, the sodium concentration at the fistula outlet is: $Cs-[(Cbi-Cbo)Qbi/Qa]$.

The magnitude of recirculation resulting when blood flow through the dialyzer is countercurrent to access flow is defined according to the following equation:

$$R = \frac{Qbi}{Qa} \quad (7)$$

where R is the dimensionless ratio of dialyzer to blood access flow rate.

Equation (7) can be rewritten as:

$$Qa = Qbi/R \quad (8)$$

When equation (8) is substituted into equation (6) and solved for CboCn, the following equation obtains:

$$CboCn = \frac{CbiCn(R+1) - CsCn}{R} \quad (9)$$

Based upon the definition of dialysance, it is possible to write:

$$JbCn = Dc[CbiCn - CdiCn] \quad (10)$$

where:
JbCn=flux of sodium ion or its surrogate Cn out of the blood;
Dc=true conductivity dialysance measured with a change in CdiCn concentrations and when arterial and venous lines are in first orientation, i.e. using the method described above in which dialysis solutions having different initial concentrations are successively flowed through the dialyzer and concentration measurements are taken upstream and downstream of the dialyzer; and
CdiCn=concentration of sodium or conductivity at dialysis solution inlet of dialyzer From mass balance across the blood compartment, the following relationship can be written:

$$JbCn = (CbiCn - CboCn)Qbi \quad (11)$$

Combining equations (10) and (11) and solving for CboCn yields:

$$CboCn = CbiCn - \frac{Dc}{Qbi}(CbiCn - CdiCn) \quad (12)$$

Combining equations (9) and (12) and solving for Cbi gives:

$$CbiCn = \frac{CsCn + R\frac{Dc}{Qbi}CdiCn}{1 + R\frac{Dc}{Qbi}} \quad (13)$$

The relationship between true conductivity dialysance (i.e., Dc) as measured using a change in CdiCn concentrations and the effective conductivity dialysance (i.e., Dc') observed when there is recirculation is:

$$\frac{Dc'}{Dc} = 1 - \frac{CbiCn2 - CbiCn1}{CdiCn2 - CdiCn1} \quad (14)$$

where:
CbiCn1 and CbiCn2=the concentration of sodium or conductivity at the dialyzer blood inlet for a first and second dialysis solution, respectively; and
CdiCn1 and CdiCn2=the concentration of sodium or conductivity at the dialyzer dialysis solution inlet for a first and second dialysis solution, respectively.

Using equation (13) to calculate the term (CbiCn2−CbiCn1) as a function of R and Dc/Qbi, gives the following relationship:

$$CbiCn2 - CbiCn1 = \frac{R(Dc/Qbi)[CdiCn2 - CdiCn1]}{1 + R(Dc/Qbi)} \quad (15)$$

Substituting equation (15) into equation (14) and simplifying gives:

$$Dc'/Dc = \frac{1}{1 + R(Dc/Qbi)} \quad (16)$$

Finally, substituting equation (7) into equation (16) and simplifying gives:

$$Qa = \frac{Dc \cdot Dc'}{Dc - Dc'} \quad (17)$$

It is also possible to rearrange equation (16) in terms of recirculation, R, giving:

$$R = Qbi(1/Dc' - 1/Dc) \quad (18)$$

Equation (17) demonstrates that it is possible to calculate blood access flow rate solely from two dialysance measurements. Similarly, it is possible to determine recirculation from equation (18). While the forgoing derivation was based on sodium ion concentration, it is important to realize that the method would work with other solutes equally as well, including, for example, dextrose, oxygen or dyes added to the dialysate. However, the embodiment wherein sodium concentrations are measured is particularly advantageous because the conductivity of dialysis fluid is primarily dependent upon sodium and chloride ion concentration; further, sodium clearance or dialysance is known to be indicative of urea clearance. Thus, it is possible to determine dialysance or clearance from conductivity measurements alone.

A first dialysance value, Dc, is measured with the arterial and venous lines in the first orientation, i.e. in the orientation in which the arterial line carries blood withdrawn from a portion of the fistula upstream of the venous line so that dialyzer blood flow is in the same direction as flow through the fistula (see for example, FIG. 4A). A second dialysance value, Dc', is measured after the lines are reconfigured and dialyzer flow is in the second orientation, i.e. in the orientation in which the arterial line withdraws blood from a position in the fistula downstream of where blood from the venous line is returned (see for example, FIG. 4B).

As noted earlier, the dialysance obtained for these two configurations can be determined in a variety of ways, including those methods described in the background section. In a preferred embodiment, however, the dialysance values are determined according to the method described above wherein dialysis solutions having different initial concentrations of a substance are successively flowed through a dialyzer during a dialysis treatment and the concentration of the substance measured upstream and downstream of the dialyzer. Referring again to FIG. 1, as the first dialysis solution is flowed through the dialyzer 38, the upstream and downstream detector 34, 46 make a first and second measurement of the concentration of the substance upstream (Cdi1) and downstream (Cdo1) of the dialyzer 38, respectively. Likewise, when second dialysis solution is flowed through the dialyzer, the upstream and downstream detector 34, 46 make a first and second measurement upstream (Cdi2) and downstream (Cdo2), respectively. Preferably, the time period between making the first measurement for the first dialysis solution (Cdi1) and the first measurement for the second dialysis solution (Cdi2) is short, most preferably, approximately three minutes or less. This ensures that any variations in blood concentrations and dialysance values is minimal.

The measured values can be relayed to the comparator 54 which may display the concentration values or calculate a concentration difference between the upstream and downstream values for each of the dialysis solutions. These values can then be used by the comparator 54 alone or in combination with a difference unit 58 to generate a dialysance value and ultimately a hemodialysis parameter according to the equations listed above. For example, the concentration measurements can be utilized according to equation (4) to determine dialysance values; the dialysance value for each orientation can then be used to calculate important hemodialysis parameters. For example, blood access flow rate can be calculated using equation (17) and recirculation can be calculated using equation (18).

The reconfiguring step of this method of the invention can be accomplished in several ways. For example, looking again at FIG. 1, the fluid conduit set 66 and the first and second transfer lines 74, 68 may be omitted. In which case, the arterial and venous lines 76, 64 may each be connected at one end to a needle/catheter 72, 70 to facilitate direct insertion of the lines into a patient's fistula 82. When needles are used, the reconfiguration process can be accomplished in at least two ways. A single needle could be withdrawn and appropriately positioned to achieve the second orientation. For example, if the arterial line 74 and its needle 72 were moved, the needle would be repositioned downstream of the venous line 64. Alternatively, both needles 72, 70 could be withdrawn from the fistula 82 and then repositioned such that the arterial line 76 withdraws blood from a downstream portion of a patient's fistula and the venous line returns blood to an upstream portion of the fistula. In the case where catheters are used, the lines may be repositioned simply by moving the arterial line 76 to the venous catheter 70 and the venous line 64 to the arterial catheter 70. Most preferably, however, the reconfiguring of the lines is facilitated through the use of the fluid conduit set 66 described above.

Importantly, this overall approach is non-invasive, unlike the prior art approaches which require the injection of solutions into a patient's blood or the insertion of intravascular sensors in order to calculate blood access flow rates.

Calculation of Hemodialysis Parameters Based Upon Urea Concentration

In the other embodiments of the invention, hemodialysis parameters are also determined from multiple dialysance measurements. However, in these embodiments, changes in urea concentrations are measured instead of changes in sodium concentration.

One embodiment in which urea concentrations are measured differs from that described above in that measurements must be made on both the blood and dialysate sides of the dialyzer, whereas the other methods of the present invention simply involved taking measurements on the dialysis solution side of the dialyzer. The mathematical basis for this method parallels that for the method based upon determining sodium concentrations. However, whereas the embodiment relying on sodium concentrations involves a technique involving a change in sodium concentration at the dialyzer inlet, such a technique is not used in the case of urea. This makes the calculation simpler but makes the method technically more difficult relative to the sodium method described above.

Based upon the sodium flow shown in FIG. 5 and its accompanying text, it is possible to show by analogy that in the case where urea concentrations are measured that:

$$CbiU = \frac{Qa \cdot CsU + CboU \cdot Qbi}{Qa + Qbi} \quad (20)$$

where:

Qa=access inlet flow rate

Qbi=dialyzer blood inlet flow rate

CbiU=concentration of urea at the dialyzer blood inlet

CsU=concentration of systemic urea

CboU=concentration of urea at the dialyzer blood outlet

The degree of recirculation resulting during reversal of the lines can be defined as:

$$R = \frac{Qbi}{Qa} \quad (21)$$

where R is the dimensionless ratio of dialyzer to access flow rates.

Equation (21) can be rewritten as:

$$Qa = Qbi/R \quad (22)$$

Substitution of equation (22) into equation (20) and solving for CboU yields:

$$CboU = \frac{CbiU(1+R) - CsU}{R} \quad (23)$$

When the ultrafiltration rate (Qf) is equal to zero, it is possible to write by definition:

$$Du = \frac{(CbiU - CboU)}{CbiU} Qbi \tag{24}$$

where Du=urea clearance or urea dialysance.
Solution of equation (24) for CboU gives:

$$CboU = (1 - [Du/Qbi])CbiU \tag{25}$$

Combining equations (23) and (25) and solving for CbiU/CsU yields:

$$CbiU/CsU = \frac{1}{(1+R) - R(1 - Du/Qbi)} \tag{26}$$

The combination of equations (23) and (25) requires steady state with respect to Cbi and Cbo. There will be a very short transient when the arterial and venous lines are first reconfigured as both Cbi and Cbo fall. Simulation with typical values shows it reaches steady state very rapidly, within 2 or 3 min, and 95% of the change occurs within the first minute.

By definition effective urea clearance or dialysance (DeU) relates to urea clearance or dialysance (Du) in accordance with the following equation:

$$DeU = Du \times \frac{CbiU}{CsU} \tag{27}$$

where:
DeU=effective urea clearance or dialysance
Du=urea clearance or dialysance
CsU=systemic urea concentration
Combining equations (26) and (27) and simplifying, gives the equation:

$$\frac{DeU}{Du} = \frac{1}{1 + R(Du/Qbi)} \tag{28}$$

By combining equation (28) with equation (22) and simplifying, it can be shown that:

$$Qa = \frac{DeU \cdot Du}{Du - DeU} \tag{29}$$

It is also possible to rearrange equation (28) in terms of recirculation, R, giving:

$$R = Qbi(1/Dc' - 1/Dc) \tag{30}$$

Thus, equations (29) and (30) demonstrate that it is possible to calculate a hemodialysis parameter such as access flow rate (Qa) and recirculation (R) from urea dialysance and effective urea dialysance.

The method of determining the dialysance values Du and DeU more specifically involve the following steps (reference made to FIG. 1):

(a) calibrating the flow rate of the blood pump 78 which pumps blood through the dialyzer 38;
(b) controlling the ultrafiltration flow rate through the dialyzer 38 so that such flow is reduced to zero;
(c) reconfiguring the arterial line 76 and the venous line 64 so that the arterial line 76 receives blood from a downstream portion of a patient's fistula and the venous line 64 returns blood to an upstream portion in a patient's fistula;
(d) waiting a period of time to allow a patient's blood to circulate after reversing the arterial and venous line 76, 64 so that the urea concentration at the dialyzer blood inlet 79 (Cbi) and at the dialyzer blood outlet 63 (Cbo) equilibrates;
(e) determining urea concentration at the dialyzer blood inlet 79 (CbiU), the dialyzer blood outlet 63 (CboU) and the dialysis solution outlet 42 (CdoU);
(f) stopping the dialysis blood pump 78 and disconnecting the arterial line 76 from the fistula 82;
(g) removing and discarding a volume of blood from the fistula 82; and
(h) obtaining a blood sample from said fistula 82 to determine a value for systemic urea concentration (CsU).

Following the above procedure, it is possible to obtain the necessary concentration values for CbiU and CboU. With these values and a knowledge of blood dialyzer flow rate, Qbi, (set by the operator), urea dialysance, Du, can be calculated according to equation (24). With a value for Du, and with knowledge of the urea concentration value at the dialyzer blood inlet (CbiU) and systemic urea concentration (CsU), it is possible to calculate DeU according to equation (27). Blood access flow rate (Qa) can then be calculated from the values for Du and DeU according to equation (29) and recirculation according to equation (30).

The step of reconfiguring the arterial and venous lines 76, 64 can be done manually or, preferably, can be automated by use of a fluid conduit set 66 as described as described the method in which sodium ion concentrations are measured. In the preferred embodiment, the step of waiting a period of time to allow Cbi and Cbo to equilibrate involves waiting approximately 5 minutes after reversal of the arterial and venous lines 76, 64, the step of removing a volume of blood from the fistula 82 comprises removing approximately 10 ml of blood and the step of obtaining a blood sample from a patient's fistula 82 is completed within 15 seconds of the step of disconnecting the arterial line 76 to avoid a rise in blood urea nitrogen (BUN) after cardiopulmonary recirculation effect is over. When samples are withdrawn to determine CbiU, CboU and CdoU, preferably the samples are all drawn within a very short time period; most preferably, the blood samples are drawn essentially simultaneously.

This embodiment of the invention (i.e., calculating hemodialysis parameters from blood urea concentrations) is technically more difficult than the embodiment wherein sodium concentrations are calculated. This is due in part to the difficulty in obtaining the sample to determine systemic urea concentrations (CsU) and problems in calculating BUN and dialysate urea concentrations with precision when the urea concentrations are low.

Another embodiment utilizes a non-invasive process similar to that described for sodium. However, in this case it is not necessary to use the approach in which two separate dialysis solutions having different initial concentrations of a substance are successively flowed through the dialyzer and measurements made upstream and downstream of the dialyzer. Instead, urea concentrations only have to measured downstream of the dialyzer, since the concentration of urea upstream of the dialyzer is zero. Thus, in this embodiment, it is possible to use the dialysis apparatus described earlier in which there is only a single downstream detector capable of measuring urea. An example of such a detector is the Baxter Biostat 1000.

In this embodiment (referring again to FIG. 1), systemic blood urea nitrogen concentration can be measured at the beginning of dialysis by either: (a) bypassing dialysate flow and creation of a high ultrafiltration rate (Qf) which flushes the dialysate compartment 38a with blood ultrafiltrate such that urea concentration is equal to blood water urea concentration or (b) closing the dialysis solution line to recirculate the dialysate compartment 38a until it reaches equilibrium with the blood compartment 38b and has urea concentration equal to the blood water urea concentration. The time required for these maneuvers is approximately 10 minutes and will be somewhat dialyzer specific depending on membrane hydraulic permeability and volume of the dialysate compartment 38a. Constants could be developed for any specific dialyzer. The equilibrated Qf will be flowing past the downstream detector 46, which in this case is specific for urea. The baseline concentration of dialysate urea nitrogen (Cdubl) can be measured and used to calculate blood urea nitrogen (Cbubl) in accordance with the following equation:

$$Cbubl = 0.94\ (Cdubl) \tag{31}$$

where 0.94 represents the plasma water fraction.

Next a single pass dialysate flow is established and after about 5 minutes the downstream detector 46 measures a baseline dialysate outlet urea concentration, Cdoubl. Baseline dialyzer urea dialysance (Dubl) can then be calculated according to the following equation:

$$Dubl = Cdoubl(Qd)/Cbubl \tag{32}$$

Equation (32) is based on the definition of urea dialysance where Cdoubl(Qd) is the rate of urea flux from blood to dialysate and Cbubl is blood concentration. Equation (32) can be rearranged to give:

$$Cbut = Cdut(Qd)/Dubl = Csut \tag{33}$$

where Cbut is blood urea concentration calculated at any time, t, using a new measured value of Cdut(Qd) and Dubl measured at baseline. When the arterial line 76 and venous line 64 are not reversed (i.e., the lines are in the first orientation), Cbut can be considered equal to the systemic blood urea nitrogen concentration, Csut. Thus from a measurement of Cdut(Qd), at any time it is possible to determine Csu.

Immediately after such a measurement, the arterial line 76 and venous line 64 can be reversed (i.e., the lines are reconfigured to the second configuration) and counter current dialyzer blood flow established. After the dialysate compartment 38a has been thoroughly flushed, generally in about 4–5 minutes (time constraints would be developed for any specific dialyzer Du and Qd), the downstream detector 46 again measures an outlet dialysate urea concentration (Cdout'), where t' is the number of minutes after the arterial line 76 and venous line 64 have been reversed to the second orientation. Effective urea clearance (Deu) can then be calculated from the equation:

$$Deut' = Cdout'(Qd)/Csut \tag{34}$$

where Csut is determined as described above using Equation 33.

All the necessary information is then available to calculate blood access flow rate according to the following equation which parallels equations (17) and (29) above:

$$Qa = Dubl \cdot Deut'/(Dubl - Deut') \tag{35}$$

Thus, with this method, it is possible to determine hemodialysis parameters with only a single downstream detector 46. Like the sodium method described earlier, this approach allows hemodialysis parameters to be measured solely from measurements made on the dialysis solution side of the dialyzer apparatus.

It is necessary to assume that urea clearance or dialysance (Du) has not changed from the DubI value measured. The value for Du may fall due to clotting or the presence of recirculation, even with cocurrent flow at the time Csut is measured. In the event that Dut' does not equal Dubl, the Qa calculation will be in error. With conductivity dialysance (Dcn), since serial values have been measured concurrently, it is known if there has been any reduction of conductivity dialysance from the baseline value.

We claim:

1. A method for determining blood access flow rate using a dialysis system including a dialyzer having a semipermeable membrane delimiting a first chamber through which blood circulates and a second chamber through which dialysis solution circulates and an arterial line and a venous line connected to an inlet and an outlet of the dialyzer, respectively, comprising:

(a) positioning said arterial line and said venous line in a first orientation, wherein said arterial line carries blood from an upstream portion of a patient's fistula and said venous line carries blood toward a downstream portion of said fistula;

(b) determining a first dialysance value for dialysis conditions in which said arterial and venous line are in said first orientation;

(c) reconfiguring said arterial and venous lines to a second orientation, wherein said arterial line carries blood from a downstream portion of said fistula and said venous line carries blood toward an upstream portion of said fistula;

(d) determining a second dialysance value for dialysis conditions in which said arterial and venous line are in said second orientation; and (e) calculating from said first and second dialysance values, a hemodialysis parameter, wherein said step of calculating includes calculating blood access flow rate according to the formula:

$$Qa = \frac{(Dc)(Dc')}{Dc - Dc'}$$

where

Qa=blood access flow rate;

Dc=the dialysance value determine when said arterial and venous line are in said first orientation; and Dc'=the dialysance value determine when said arterial and venous line are in said second orientation.

2. A method for determining blood access flow rate using a dialysis system including a dialyzer having a semipermeable membrane delimiting a first chamber through which blood circulates and a second chamber through which dialysis solution circulates and an arterial line and a venous line connected to an inlet and an outlet of a dialyzer, respectively, comprising:

(a) positioning said arterial line and said venous line in a first orientation, wherein said arterial line carries blood from an upstream portion of a patient's fistula and said venous line carries blood toward a downstream portion of said fistula;

(b) determining a first dialysance value for dialysis conditions in which said arterial and venous line are in said first orientation;

(c) reconfiguring said arterial and venous lines to a second orientation, wherein said arterial line carries blood from a downstream portion of said fistula and said venous line carries blood toward an upstream portion of said fistula;

(d) determining a second dialysance value for dialysis conditions in which said arterial and venous line are in said second orientation; and (e) calculating from said first and second dialysance values, a hemodialysis parameter, wherein said step of determining a first and second dialysance value each include making a measurement of the concentration of a substance in a dialysis solution downstream of said second chamber, and wherein said step of calculating includes calculating blood access flow rate according to the formula:

$$Qa = \frac{(Dc)(Dc')}{Dc - Dc'}$$

where

Qa=blood access flow rate;

Dc=the dialysance value determine when said arterial and venous line are in said first orientation; and Dc'=the dialysance value determine when said arterial and venous line are in said second orientation.

3. A method for determining recirculation using a dialysis system including a dialyzer having a semipermeable membrane delimiting a first chamber through which blood circulates and a second chamber through which dialysis solution circulates and an arterial line and a venous line connected to an inlet and an outlet of the dialyzer, respectively, comprising:

(a) positioning said arterial line and said venous line in a first orientation, wherein said arterial line carries blood from an upstream portion of a patient's fistula and said venous line carries blood toward a downstream portion of said fistula;

(b) determining a first dialysance value for dialysis conditions in which said arterial and venous line are in said first orientation;

(c) reconfiguring said arterial and venous lines to a second orientation, wherein said arterial line carries blood from a downstream portion of said fistula and said venous line carries blood toward an upstream portion of said fistula;

(d) determining a second dialysance value for dialysis conditions in which said arterial and venous lines are in said second orientation; and (e) calculating from said first and second dialysance values, a hemodialysis parameter, wherein said step of calculating includes calculating recirculation according to the formula:

$$R = Qbi(1/Dc' - 1/DC)$$

where

R=recirculation;

Qbi=dialyzer blood inlet flow rate;

Dc=the dialysance value determined when said arterial and venous line are in said first orientation; and Dc'=the dialysance value determine when said arterial and venous line are in said second orientation.

4. A method of determining recirculation using a dialysis system including a dialyzer having a semipermeable membrane delimiting a first chamber through which blood circulates and a second chamber through which dialysis solution circulates and an arterial line and a venous line connected to an inlet and an outlet of the dialyzer, respectively, comprising:

(a) positioning said arterial line and said venous line in first orientation, wherein said arterial line carries blood from an upstream portion of a patient's fistula and said venous line carries blood toward a downstream portion of said fistula;

(b) determining a first dialysance value for dialysis conditions in which said arterial and venous line are in said first orientation;

(c) reconfiguring said arterial and venous lines to a second orientation, wherein said arterial line carries blood from a downstream portion of said fistula;

(d) determining a second dialysance value for dialysis conditions in which said arterial and venous line are in said second orientation; and (e) calculating from said first and second dialysance values, a hemodialysis parameter, wherein said step of determining a first and second dialysance value each include making a measurement of the concentration of a substance in a dialysis solution downstream of said second chamber, and wherein said step of calculating includes calculating recirculation according to the formula:

$$R = Qbi(1/Dc' - 1/Dc)$$

where

R=recirculation

Qbi=dialyzer blood inlet flow rate;

Dc=the dialysance value determined when said arterial and venous line are in said first orientation; and Dc'=the dialysance value determined when said arterial and venous line are in said second orientation.

5. A method for determining a hemodialysis parameter in a dialysis system including a dialyzer having a semipermeable membrane delimiting a first chamber through which blood is circulated by a dialysis blood pump and a second chamber through which dialysis solution circulates and an arterial and venous line connected to an inlet and outlet of said first chamber, respectively, comprising:

(a) determining urea dialysance and effective urea dialysance; and (b) calculating a hemodialysis parameter from said urea dialysance and said effective urea dialysance, wherein said step of determining urea dialysance and effective urea dialysance comprises:

(i) reconfiguring said arterial line and venous line from a first orientation, wherein said arterial line carries blood from an upstream portion of a patient's fistula and said venous line carries blood to a downstream portion in said fistula, to a second orientation, wherein said arterial line carries blood from a downstream portion of a patient's fistula and said venous line carries blood to an upstream portion in said fistula;

(ii) determining a concentration of urea at said first chamber inlet (CbiU), a concentration of urea at said first chamber outlet (CboU), and a concentration of urea downstream of said second chamber (CboU); and (iii) determining a systemic urea concentration (CsU); and wherein said step of determining urea dialysance and effective urea dialysance further comprises:

(x) calculating a value for urea dialysance according to the formula:

$$Du = \frac{(CbiU - CboU)}{CbiU} Qbi;$$

and (y) calculating a value for effective urea dialysance according to the formula:

$$DeU = \frac{(CbiU)}{CsU} Du$$

where
Du=urea dialysance;
DeU=effective urea dialysance;
CbiU=concentration of urea at said dialyzer blood inlet;
CboU=concentration of urea at said dialyzer blood outlet;
CsU=concentration of systemic urea; and
Qbi=dialyzer blood inlet flow rate.

6. A method for determining a hemodialysis parameter in a dialysis system including a dialyzer having a semipermeable membrane delimiting a first chamber through which blood is circulated by a dialysis blood pump and a second chamber through which dialysis solution circulates and an arterial and venous line connected to an inlet and outlet of said first chamber, respectively, comprising:

(a) determining urea dialysance and effective urea dialysance; and (b) calculating a hemodialysis parameter form said urea dialysance and said effective urea dialysance, wherein said step of determining urea dialysance and effective urea dialysance comprises:

(i) reconfiguring said arterial line and venous line from a first orientation, wherein said arterial line carries blood from an upstream portion of a patient's fistula and said venous line carries blood to a downstream portion in said fistula, to a second orientation, wherein said arterial line carries blood from a downstream portion of a patient's fistula and said venous line carries blood to an upstream portion in said fistula;

(ii) determining a concentration of urea at said first chamber inlet (CbiU), a concentration of urea at first chamber outlet (CboU), and a concentration of urea downstream of said second chamber (CdoU); and (iii) determining a systemic urea concentration (CsU), and wherein said step of determining urea dialysance and effective urea dialysance further includes:

(x) calculating a value for urea dialysance according to the formula:

$$Du = \frac{(CbiU - CboU)}{CbiU} Qbi; \text{ and}$$

(y) calculating a value for effective urea dialysance according to the formula:

$$DeU = \frac{CbiU}{CsU} Du$$

where
Du=urea clearance dialysance;
DeU=effective urea dialysance;
CbiU=concentration of urea at said dialyzer blood inlet;
CboU=concentration of urea at said dialyzer blood outlet;
CsU=concentration of systemic urea; and
Qbi=dialyzer blood inlet flow rate.

7. The method as described in claim 6, wherein said hemodialysis parameter is blood access flow rate and said step of calculating includes calculating blood access flow rate according to the equation:

$$Qa = \frac{(DeU)(Du)}{Du - DeU}$$

where
Qa=blood access flow rate;
DeU=effective urea dialysance; and
Du=urea clearance dialysance.

8. A method for determining recirculation in a dialysis system including a dialyzer having a semipermeable membrane delimiting a first camber through which blood is circulated by a dialysis blood pump and a second chamber through which dialysis solution circulates and an arterial and venous line connected to an inlet and outlet of said first chamber, respectively, comprising:

(a) determining urea dialysance and effective urea dialysance; and (b) calculating a hemodialysis parameter from said urea dialysance and said effective urea dialysance, wherein said step of calculating includes calculating recirculation according to the equation:

$$R = Qbi(1/DeU - 1/Du)$$

where
R=recirculation;
Qbi=dialyzer blood inlet flow rate;
DeU=effective urea dialysance; and
Du=urea clearance dialysance.

9. The method as described in claim 6, wherein said hemodialysis parameter is recirculation and said step of calculating includes calculating recirculation according to the equation:

$$R = Qbi(1/DeU - 1/Du)$$

where
R=recirculation;
Qbi=dialyzer blood inlet flow rate;
DeU=effective urea dialysance; and
Du=urea clearance dialysance.

* * * * *